(12) United States Patent
Woodruff et al.

(10) Patent No.: US 8,632,455 B2
(45) Date of Patent: Jan. 21, 2014

(54) GASTRIC BAND WITH ASYMMETRICAL MEMBER

(75) Inventors: Scott A. Woodruff, Cincinnati, OH (US); Gary W. Knight, West Chester, OH (US); Andrew T. Beckman, Cincinnati, OH (US); Michael J. Vendely, Lebanon, OH (US); Edward G. Chekan, Cincinnati, OH (US); Craig D. Stover, Williamston, MI (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 385 days.

(21) Appl. No.: 12/944,853

(22) Filed: Nov. 12, 2010

(65) Prior Publication Data

US 2012/0123195 A1    May 17, 2012

(51) Int. Cl.
*A61F 2/04* (2013.01)
(52) U.S. Cl.
USPC ............................................................ 600/37
(58) Field of Classification Search
USPC .................................... 600/29–31, 37, 38–40
See application file for complete search history.

(56) References Cited

U.S. PATENT DOCUMENTS

| | | | | |
|---|---|---|---|---|
| 4,969,474 | A * | 11/1990 | Schwarz | 128/885 |
| 5,312,431 | A * | 5/1994 | McEwen | 606/202 |
| 5,382,184 | A * | 1/1995 | DiForte, Jr. | 441/108 |
| 6,067,991 | A | 5/2000 | Forsell | |
| 6,461,292 | B1 | 10/2002 | Forsell | |
| 6,470,892 | B1 | 10/2002 | Forsell | |
| 7,416,528 | B2 | 8/2008 | Crawford et al. | |
| 7,442,165 | B2 | 10/2008 | Forsell | |
| 7,530,943 | B2 | 5/2009 | Lechner | |
| 7,621,863 | B2 | 11/2009 | Forsell | |
| 7,699,770 | B2 | 4/2010 | Hassler, Jr. et al. | |
| 7,775,215 | B2 | 8/2010 | Hassler, Jr. et al. | |
| 7,850,660 | B2 | 12/2010 | Uth et al. | |
| 2002/0087105 | A1 * | 7/2002 | Grosso | 602/13 |

(Continued)

FOREIGN PATENT DOCUMENTS

EP    1 547 549    6/2005
FR    2 929 842    10/2009

OTHER PUBLICATIONS

International Search Report dated Apr. 18, 2012 for Application No. PCT/US2011/059959.

(Continued)

*Primary Examiner* — Christine Matthews
*Assistant Examiner* — Joshua D Lannu
(74) *Attorney, Agent, or Firm* — Frost Brown Todd LLC (57) ABSTRACT

An apparatus comprises a strap and an inflatable bladder secured to the strap. The apparatus is sized and configured to wrap along a first plane to encompass an anatomical feature such as an esophagus or stomach. The bladder may have a cross-sectional profile that is asymmetric about the first plane, such as a tapered profile or a contoured profile. The wall thickness of the bladder may be substantially uniform or may vary about the perimeter of the bladder. The bladder may include an expansion section that allows the bladder to transition from having a substantially flat cross-sectional configuration in a non-inflated state to having a substantially tapered cross-sectional configuration an inflated state. The expansion section may include folds, pleats, gussets, or the like. The strap may have a cross-sectional profile that is asymmetric about the first plane. Such a strap may include annular ribs of varying sizes.

9 Claims, 8 Drawing Sheets

(56) References Cited

U.S. PATENT DOCUMENTS

| | | |
|---|---|---|
| 2005/0283118 A1 | 12/2005 | Uth et al. |
| 2006/0129027 A1 | 6/2006 | Catona |
| 2006/0183967 A1* | 8/2006 | Lechner .......................... 600/37 |
| 2006/0199997 A1 | 9/2006 | Hassler, Jr. et al. |
| 2008/0294180 A1 | 11/2008 | Frering et al. |
| 2009/0198261 A1 | 8/2009 | Schweikert |

OTHER PUBLICATIONS

English Abstract and Machine Translation of French Patent Application No. FR 2 929 842.

* cited by examiner

GASTRIC BAND WITH ASYMMETRICAL MEMBER

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein. Yet another example of an adjustable gastric band is disclosed in U.S. Pat. No. 7,530,943, entitled "Adjustable Stomach Band," issued May 12, 2009, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, issued as U.S. Pat. No. 7,775,215 on Aug. 17, 2010, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, issued as U.S. Pat. No. 7,699,770 on Apr. 20, 2010, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, issued as U.S. Pat. No. 8,016,745 on Sep. 13, 2011, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIGS. 1-6 illustrate an exemplary gastric band system (10). As shown, gastric band system (10) comprises an injection port (12), a gastric band (20), and a catheter (18). Injection port (12) of the present example comprises a port housing (14) and a needle penetrable septum (16). Port housing (14) defines a fluid reservoir (not shown), such that a needle may pierce septum (16) to reach the reservoir and add or withdraw fluid (e.g., saline, etc.) as described in greater detail below. Port housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, issued as U.S. Pat. No. 7,850,660 on Dec. 14, 2010, the disclosure of which is incorporated by reference herein. Alternatively, injection port (12) may have any other suitable configuration and/or operability.

Figure 1:
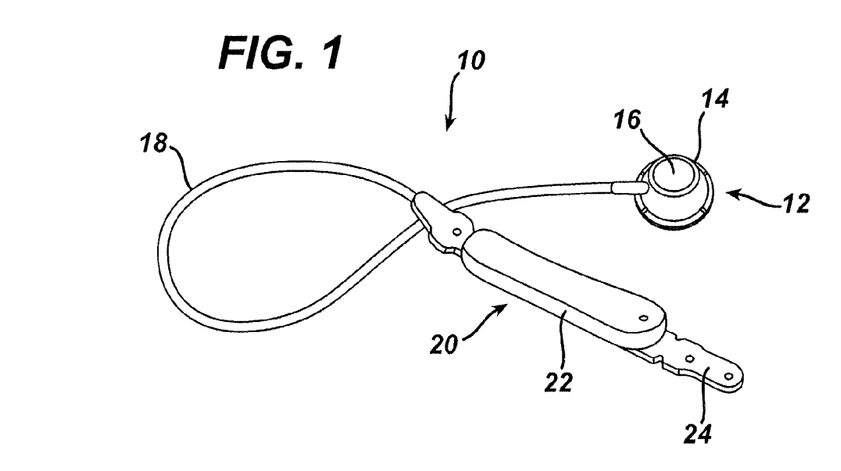
FIG. 1 depicts a perspective view of an implantable portion of an exemplary gastric band system.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). In the present example, catheter (18), bladder (22), and injection port (12) form a closed fluid circuit. Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
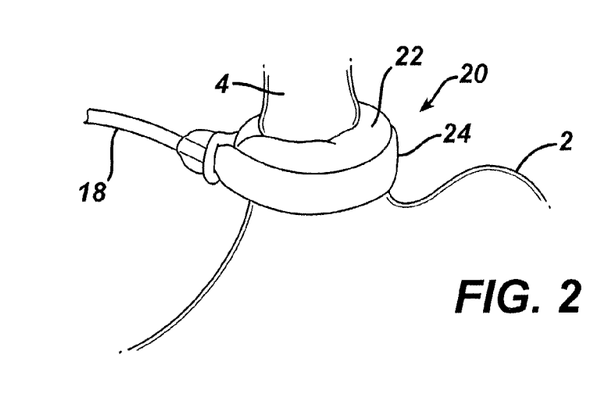
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastroesophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
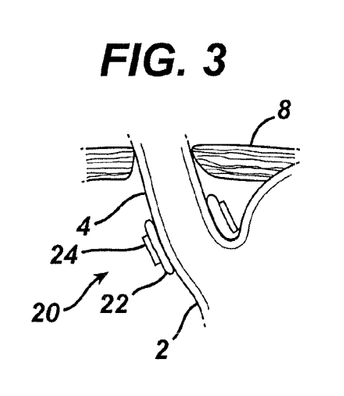
FIG. 3 depicts a cross-sectional view of the gastric band of FIG. 1, showing the band positioned around the gastro-esophageal junction of a patient in a deflated configuration.
Figure 4:
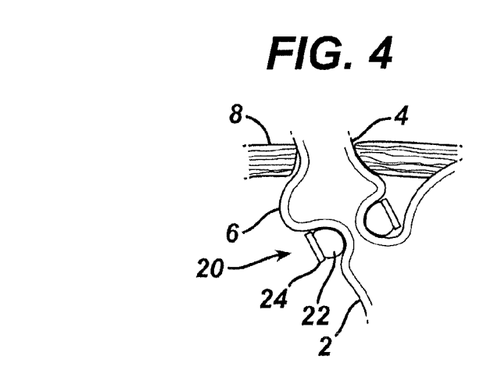
FIG. 4 depicts a cross-sectional view of the gastric band of FIG. 1, showing the band positioned around the gastro-esophageal junction of a patient in an inflated configuration to create a food intake restriction.
Figure 5A:
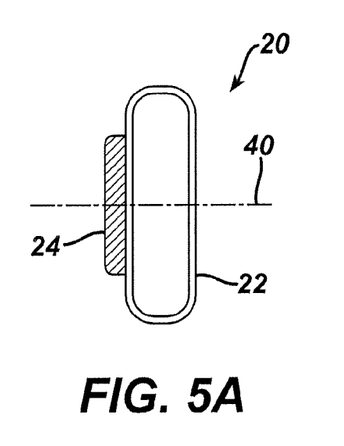
FIG. 5A depicts a cross-sectional view of the gastric band of FIG. 1, showing the gastric band having a generally symmetric profile, in a substantially non-inflated configuration.

As shown in FIGS. 2-4 and 6, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 5A also shows gastric band (20) in substantially deflated configuration. FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient. FIG. 5A also shows gastric band (20) in a substantially inflated configuration.

Figure 5B:
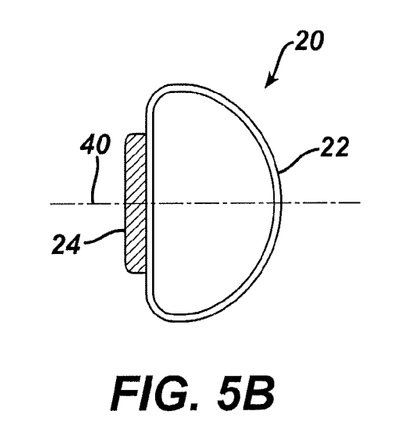
FIG. 5B depicts a cross-sectional view of the gastric band of FIG. 5A, in a substantially inflated configuration.
Figure 6:
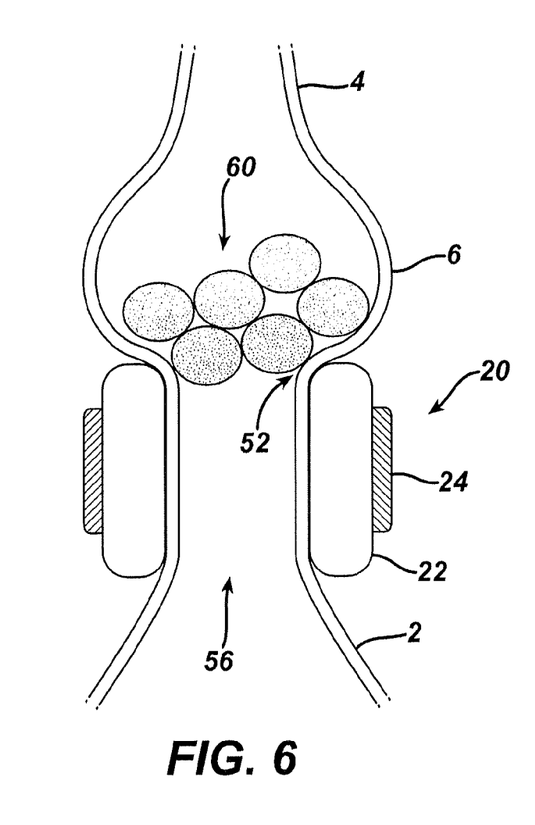
FIG. 6 depicts a cross-sectional view of the gastric band of FIG. 5A installed at the gastro-esophageal junction of a patient.

As best seen in FIGS. 5A-5B, bladder (22) of the present example is substantially symmetric about a horizontal plane (40) that bisects gastric band (20). In other words, the portion of gastric band (20) above horizontal plane (40) is substantially symmetric with the portion of gastric band (20) below horizontal plane (40). As best seen in FIG. 6, this configuration in some instances may provide a relatively abrupt transition from esophagus (4) to stomach (2). In particular, FIG. 6 illustrates a stoma passageway (56) between upper pouch (6) and stomach (2). Stoma passageway (56) has a substantially uniform width along its length, generally defined by the overall height of gastric band (20), with a relatively sharp corner (52) being formed about the upper perimeter of stoma passageway (56). Normal peristalsis during food consumption may create substantial forces at corner (52) as the esophagus (4) tries to drive food (60) downward. Such a configuration of these anatomical features may produce undesirable results in some instances, such as sialemesis, regurgitation, bad breath, irritation of the mucous membrane, weakening of the esophagus (4), undesirable dilation of the esophagus (4), and/or other results. These results may be due in part to the prolonged presence of food (60) in upper pouch (6), with such a prolonged presence being caused by the relatively highly restrictive configuration of anatomical features shown in FIG. 6.

While a purpose of a gastric band (20) may be to restrict the flow of food from esophagus (4) to stomach (2), it may be desirable in some instances to provide such a restriction in a manner that does not prolong the presence of food (60) in upper pouch (6) to a point where undesirable results occur. Put another way, it may be desirable to provide a transition from esophagus (4) to stomach (2) that is relatively smoother than the transition shown in FIG. 6. As described in greater detail below, the prolongation of food (60) presence in upper pouch (6) may be optimized by changing the configuration of gastric band (20) to the point where undesirable results are minimized if not eliminated; while the patient still feels an early sense of satiation sufficient to result in weight loss. Various examples of alternative gastric band configurations are shown in FIGS. 7A-17 and are described in greater detail below, while other alternative gastric band configurations will be apparent to those of ordinary skill in the art in view of the teachings herein. It should be understood that any of the gastric bands shown in FIGS. 7A-17 may be readily incorporated into gastric band system (10) as a substitute for gastric band (20) described above. It should also be understood that any of the gastric bands shown in FIGS. 7A-17 may alternatively be incorporated into various other types of gastric band systems, as will be apparent to those of ordinary skill in the art in view of the teachings herein.

Figure 7A:
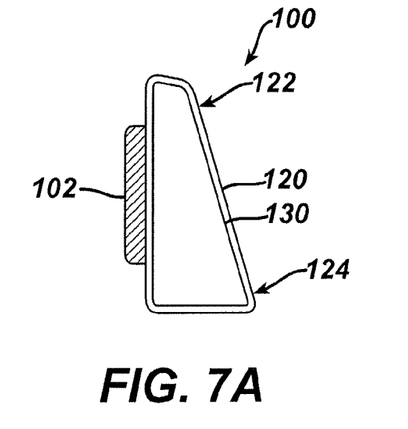
FIG. 7A depicts a cross-sectional view of an exemplary gastric band having a generally asymmetric profile and a substantially uniform wall thickness, in a substantially non-inflated configuration.
Figure 7B:
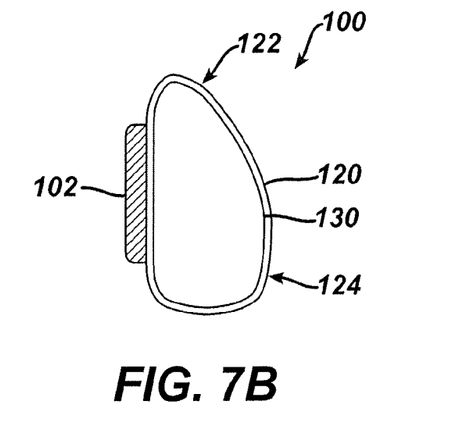
FIG. 7B depicts a cross-sectional view of the gastric band of FIG. 7A, in a substantially inflated configuration.
Figure 8:
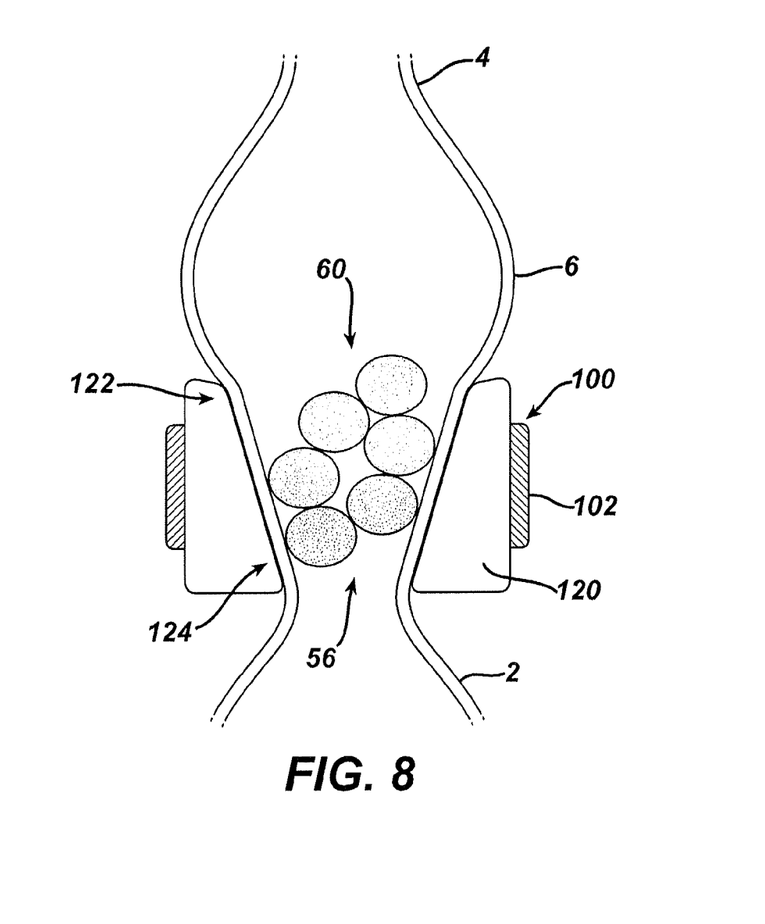
FIG. 8 depicts a cross-sectional view of the gastric band of FIG. 7A installed at the gastro-esophageal junction of a patient.

FIGS. 7A-8 depict an exemplary alternative gastric band (100) having a substantially asymmetric configuration. Gastric band (100) of this example comprises a flexible strap (102) and a bladder (120). Strap (102) is substantially similar to strap (24) described above, such that the ends of strap (102) may be secured relative to each other when gastric band (100) is sufficiently wrapped about the patient's stomach (2). For instance, strap (102) may include buckle features similar to those described in U.S. Pat. No. 7,416,528, entitled "Latching Device for Gastric Band," issued Aug. 26, 2008, the disclosure of which is incorporated by reference herein. In addition, while strap (102) is flexible in this example, strap (102) substantially resists stretching along its length, such that bladder (120) expands and exerts inward forces on the gastro-esophageal junction of the patient when fluid is added to bladder (120) (e.g., using a needle inserted through septum (16) of injection port (12), etc.). Of course, strap (102) may have any other suitable configuration.

Bladder (120) comprises a wall (130) that has a substantially uniform thickness, though this thickness may vary as described in greater detail below. Bladder (120) of the present example is substantially asymmetric about a horizontal plane (not shown) that bisects gastric band (100). In particular, an upper portion (122) of gastric band (100) presents a profile that is substantially narrower than the profile presented by a lower portion (124) of gastric band (100). This provides a generally tapered configuration. Bladder (120) is preformed to have this configuration, such that gastric band (100) presents a tapered configuration both when bladder (120) is substantially non-inflated (as seen in FIG. 7A) and when bladder (120) is substantially inflated (as seen in FIG. 7B).

FIG. 8 shows gastric band (100) installed at the gastro-esophageal junction of a patient. In comparison to the configuration shown in FIG. 6, the tapered configuration of gastric band (100) may provide a transition from esophagus (4) to stomach (2) that is relatively smoother than the transition from esophagus (4) to stomach (2) provided by gastric band (20). The stoma passageway (56) in this example has a tapered configuration complementing the tapered configuration of gastric band (100), such that corner (52) is substantially eliminated; and the angled wall defined between upper and lower portions (122, 124) helps guide food (60) through the narrowest part of the restriction formed by lower portion (124) in a relatively smooth fashion. As food (60) backs up in pouch (6), the lower parts of the sides of pouch (6) are supported by gastric band (100). In some settings, the tapered configuration of gastric band (100) and appurtenant smoothing of the transition from esophagus (4) to stomach (2) may substantially reduce the likelihood of gastric band (100) causing sialemesis, regurgitation, bad breath, irritation of the mucous membrane, weakening of the esophagus (4), undesirable dilation of the esophagus (4), undesirable dilation of pouch (6), and/or other results that may be deemed undesirable. Furthermore, the tapered configuration of gastric band (100) and appurtenant smoothing of the transition from esophagus (4) to stomach (2) may result in a relatively earlier and longer lasting sense of satiety in the patient than might otherwise be achieved by gastric band (20).

It should also be understood that the "V" shape or funnel shape provided by gastric band (100) may result in the primary point of restriction (56) being formed by lower portion (124) of gastric band (100), with upper portion (122) of gastric band (100) providing lateral structural support for the adjacent region of stomach (2) at an area where food (60), etc., may sit and produce the most force on stomach (2). As can be best seen by comparing FIG. 6 to FIG. 8, as FIG. 6 shows food (60) extending pouch (6) outwardly and creating a tight radius at corner (52); whereas FIG. 8 shows band (100) structurally supporting stomach (2) adjacent to the primary point of restriction (56). This lateral structural support may reduce complications such as permanent stretching of pouch (6). Such permanent stretching may otherwise render a gastric band ineffective at producing early satiety. Other complications that may be reduced by the lateral structural support provided by gastric band may include erosion of band (20) and/or stomach (6) at corner (52), etc. Thus, the lateral structural support provided by the funnel like configuration of band (100) may allow the stoma restriction (56) to be adjusted for more restriction with relatively fewer complications than might otherwise be obtained with band (20).

Other suitable ways in which gastric band (100) may be formed will be apparent to those of ordinary skill in the art in view of the teachings herein.

Figure 9A:
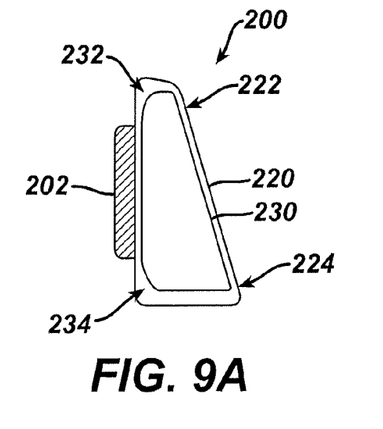
FIG. 9A depicts a cross-sectional view of an exemplary gastric band having a generally asymmetric profile and a varying wall thickness, in a substantially non-inflated configuration.
Figure 9B:
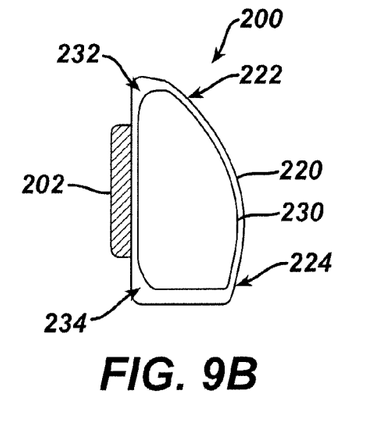
FIG. 9B depicts a cross-sectional view of the gastric band of FIG. 9A, in a substantially inflated configuration.

FIGS. 9A-9B show a merely illustrative variation of gastric band (100). The exemplary gastric band (200) shown in FIGS. 9A-9B is substantially similar to gastric band (100) shown in FIGS. 7A-8. In particular, gastric band (200) comprises a flexible strap (202) and a bladder (220). The ends of strap (202) may be secured relative to each other when gastric band (200) is sufficiently wrapped about the patient's stomach (2). For instance, strap (202) may include buckle features similar to those described in U.S. Pat. No. 7,416,528, entitled "Latching Device for Gastric Band," issued Aug. 26, 2008, the disclosure of which is incorporated by reference herein. In addition, while strap (202) is flexible in this example, strap (202) substantially resists stretching along its length, such that bladder (220) expands and exerts inward forces on the gastro-esophageal junction of the patient when fluid is added to bladder (220) (e.g., using a needle inserted through septum (16) of injection port (12), etc.). Of course, strap (202) may have any other suitable configuration.

Like bladder (120) described above, bladder (220) of the present example is also substantially asymmetric about a horizontal plane (not shown) that bisects gastric band (200). In particular, an upper portion (222) of gastric band (200) presents a profile that is substantially narrower than the profile presented by a lower portion (224) of gastric band (200). This provides a generally tapered configuration. Bladder (220) is preformed to have this configuration, such that gastric band (200) presents a tapered configuration both when bladder (220) is substantially non-inflated (as seen in FIG. 9A) and when bladder (220) is substantially inflated (as seen in FIG. 9B). Unlike bladder (120), bladder (220) of this example comprises a wall (230) having a varied thickness. In particular, wall (230) is thicker at outer corners (232, 234) than it is in other regions. Such added thickness may improve the structural integrity of bladder (220). Selectively varying the thickness of wall (230) may also isolate certain areas of wall (230) for expansion as fluid is added to bladder (220), such that the thinner regions of wall (230) will stretch in response to increased fluid pressure while thicker regions of wall (230) will stretch less or not at all as fluid pressure is increased. It should also be understood that the varied thickness of wall (230) may control expansion of stomach (2) during peristaltic contractions of swallowing/digestion. With focused areas for expansion, bladder (220) may respond to such forces by expanding in the path of least resistance. Of course, other regions of wall (230) may have increased thickness, in addition to or in lieu of either or both corners (232, 234) having increased thickness. Other suitable ways in which gastric band (200) may be formed will be apparent to those of ordinary skill in the art in view of the teachings herein.

Figure 10A:
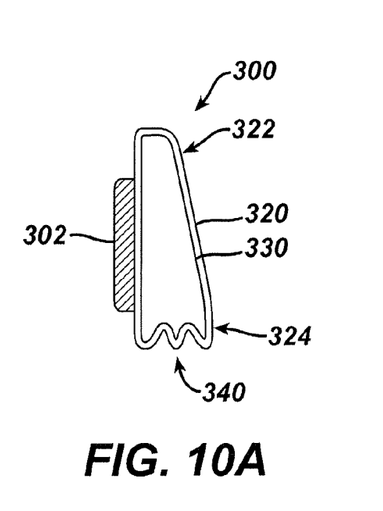
FIG. 10A depicts a cross-sectional view of an exemplary gastric band having a generally asymmetric profile, a substantially uniform wall thickness, and an expansion section, in a substantially non-inflated configuration.
Figure 10B:
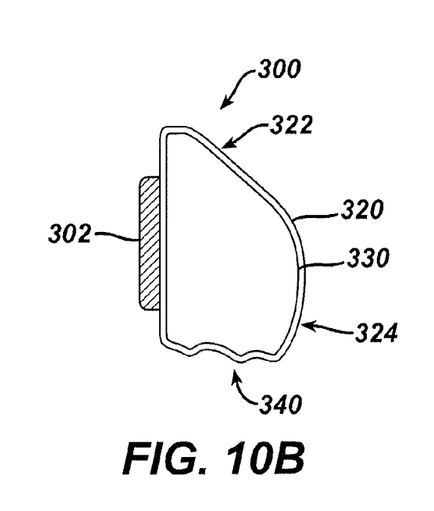
FIG. 10B depicts a cross-sectional view of the gastric band of FIG. 10A, in a substantially inflated configuration.

FIGS. 10A-10B show another merely illustrative variation of gastric band (100). The exemplary gastric band (300) shown in FIGS. 10A-10B is substantially similar to gastric band (100) shown in FIGS. 7A-8. In particular, gastric band (300) comprises a flexible strap (302) and a bladder (320). The ends of strap (302) may be secured relative to each other when gastric band (300) is sufficiently wrapped about the patient's stomach (2). For instance, strap (302) may include buckle features similar to those described in U.S. Pat. No. 7,416,528, entitled "Latching Device for Gastric Band," issued Aug. 26, 2008, the disclosure of which is incorporated by reference herein. In addition, while strap (302) is flexible in this example, strap (302) substantially resists stretching along its length, such that bladder (320) expands and exerts inward forces on the gastro-esophageal junction of the patient when fluid is added to bladder (320) (e.g., using a needle inserted through septum (16) of injection port (12), etc.). Of course, strap (302) may have any other suitable configuration.

Like bladder (120) described above, bladder (320) comprises a wall (330) having a substantially uniform thickness. Bladder (320) of the present example is also substantially asymmetric about a horizontal plane (not shown) that bisects gastric band (300). In particular, when bladder (320) is inflated, an upper portion (322) of gastric band (300) presents a profile that is substantially narrower than the profile presented by a lower portion (324) of gastric band (300). This provides a generally tapered configuration. Unlike bladder (120), bladder (320) of this example comprises an expansion section (340), which is formed like a bellows. Expansion section (340) is configured to facilitate transition of bladder (320) from a substantially flat configuration when bladder (320) is substantially non-inflated (as seen in FIG. 10A) to a substantially tapered configuration when bladder (320) is substantially inflated (as seen in FIG. 10B). Expansion section (340) may include a variety of types of structural features, including but not limited to folds, pleats, gussets, etc.

Other suitable ways in which gastric band (300) may be formed will be apparent to those of ordinary skill in the art in view of the teachings herein.

Figure 11A:
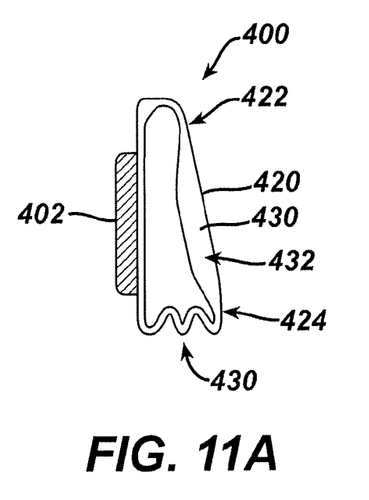
FIG. 11A depicts a cross-sectional view of an exemplary gastric band having a generally asymmetric profile, a varying wall thickness, and an expansion section, in a substantially non-inflated configuration.
Figure 11B:
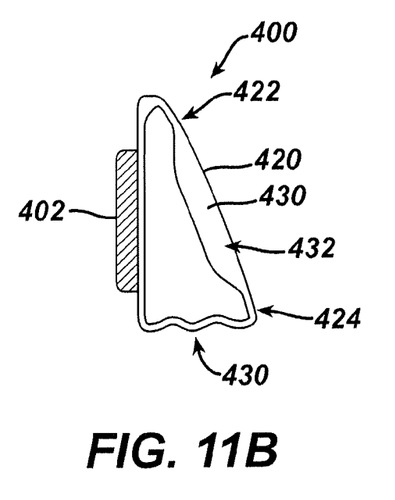
FIG. 11B depicts a cross-sectional view of the gastric band of FIG. 11A, in a substantially inflated configuration.

FIGS. 11A-11B show a merely illustrative variation of gastric band (300). The exemplary gastric band (400) shown in FIGS. 11A-11B is substantially similar to gastric band (300) shown in FIGS. 10A-10B. In particular, gastric band (400) comprises a flexible strap (402) and a bladder (420). The ends of strap (402) may be secured relative to each other when gastric band (400) is sufficiently wrapped about the patient's stomach (2). For instance, strap (402) may include buckle features similar to those described in U.S. Pat. No. 7,416,528, entitled "Latching Device for Gastric Band," issued Aug. 26, 2008, the disclosure of which is incorporated by reference herein. In addition, while strap (402) is flexible in this example, strap (402) substantially resists stretching along its length, such that bladder (420) expands and exerts inward forces on the gastro-esophageal junction of the patient when fluid is added to bladder (420) (e.g., using a needle inserted through septum (16) of injection port (12), etc.). Of course, strap (402) may have any other suitable configuration.

Bladder (420) of the present example is also substantially asymmetric about a horizontal plane (not shown) that bisects gastric band (400). In particular, when bladder (420) is inflated, an upper portion (422) of gastric band (400) presents a profile that is substantially narrower than the profile presented by a lower portion (424) of gastric band (400). This provides a generally tapered configuration. Bladder (420) of this example also comprises an expansion section (440), which is formed like a bellows. Expansion section (440) is configured to facilitate transition of bladder (420) from a substantially flat configuration when bladder (420) is substantially non-inflated (as seen in FIG. 11A) to a substantially tapered configuration when bladder (420) is substantially inflated (as seen in FIG. 11B). Expansion section (440) may include a variety of types of structural features, including but not limited to folds, pleats, gussets, etc.

Unlike bladder (320), bladder (420) of this example comprises a wall (430) having a varied thickness. In particular, wall (430) is thicker at inner region (432) than it is in other regions. Such added thickness may improve the structural integrity of bladder (420). Selectively varying the thickness of wall (430) may also isolate certain areas of wall (430) for expansion as fluid is added to bladder (420), such that the thinner regions of wall (430) will stretch in response to increased fluid pressure while thicker regions of wall (430) will stretch less or not at all as fluid pressure is increased. It should also be understood that the varied thickness of wall (430) may control expansion of stomach (2) during peristaltic contractions of swallowing/digestion. With focused areas for expansion, bladder (420) may respond to such forces by expanding in the path of least resistance. Of course, other regions of wall (430) may have increased thickness, in addition to or in lieu of inner region (432) having increased thickness. Other suitable ways in which gastric band (400) may be formed will be apparent to those of ordinary skill in the art in view of the teachings herein.

Figure 12:
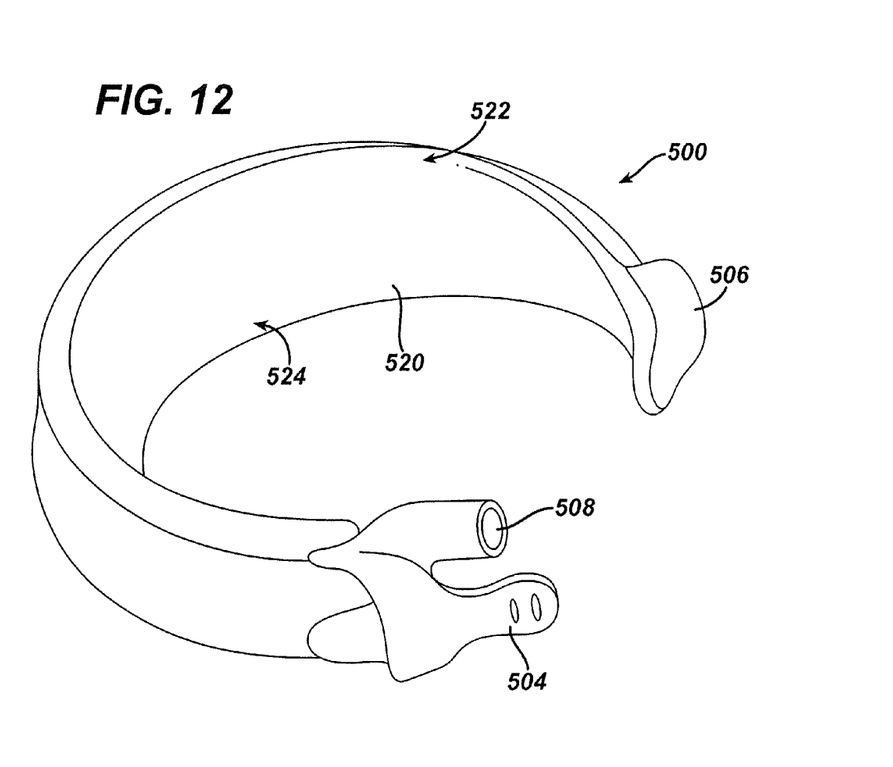
FIG. 12 depicts a perspective view of an exemplary gastric band having a generally asymmetric profile defined by a contoured contact surface with a lower portion that is thicker than an upper portion.
Figure 13:
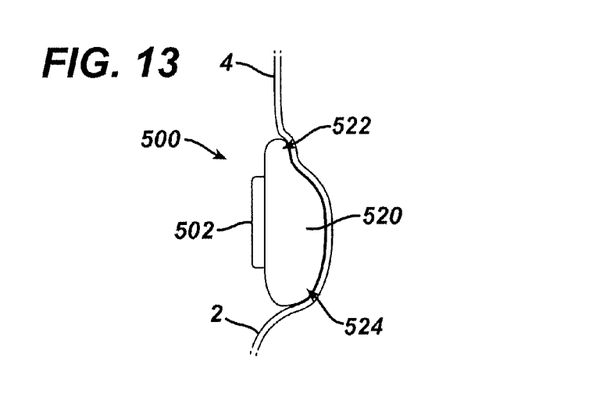
FIG. 13 depicts a cross-sectional view of the gastric band of FIG. 12.

Yet another merely illustrative gastric band (500) is shown in FIGS. 12-13. Gastric band (500) of this example comprises a flexible strap (502) (not shown in FIG. 12) and a bladder (520). Each end of strap (502) includes a respective buckle member (504, 506), which may be secured to each other when gastric band (500) is sufficiently wrapped about the patient's stomach (2). For instance, buckle members (504, 506) may be constructed an operable in accordance with the teachings of U.S. Pat. No. 7,416,528, entitled "Latching Device for Gastric Band," issued Aug. 26, 2008, the disclosure of which is incorporated by reference herein. Buckle member (504) also includes an integral fluid port (508), which is in fluid communication with the interior of bladder (520) and may be coupled with catheter (18). In addition, while strap (502) is flexible in this example, strap (502) substantially resists stretching along its length, such that bladder (520) expands and exerts inward forces on the gastro-esophageal junction of the patient when fluid is added to bladder (520) (e.g., using a needle inserted through septum (16) of injection port (12), etc.). Of course, strap (502) may have any other suitable configuration.

Like various bladders described above, bladder (520) of the present example is also substantially asymmetric about a horizontal plane (not shown) that bisects gastric band (500). In particular, an upper portion (522) of gastric band (500) presents a profile that is substantially narrower than the profile presented by a lower portion (524) of gastric band (500), such that the stoma passageway provided by gastric band (500) between esophagus (4) and stomach (2) is wider near the top of gastric band (500) (i.e., the esophagus (4) side) than it is near the bottom of gastric band (500) (i.e., the stomach (2) side). Unlike various bladders described above, and as best seen in FIG. 13, upper and lower portions (522, 524) present a contoured configuration rather than a generally tapered configuration. In some versions, upper portion (522) is generally flat or even concave while lower portion (524) is generally convex, with a curved transition being provided between upper and lower portions (522, 524). Bladder (520) is preformed to have a "bottom heavy" contoured configuration in the present example, such that gastric band (500) presents the contoured configuration both when bladder (520) is substantially non-inflated (as seen in FIG. 12) and when bladder (520) is substantially inflated (as seen in FIG. 13). In some settings, the contoured configuration of bladder (520) may provide results similar to those that may be provided by the tapered configuration of bladders (120, 220, 320, 420) described above, such as the reduction or elimination of sialemesis, regurgitation, bad breath, irritation of the mucous membrane, weakening of the esophagus (4), undesirable dilation of the esophagus (4), and/or other results that may be deemed undesirable. Other suitable ways in which gastric band (500) may be formed will be apparent to those of ordinary skill in the art in view of the teachings herein.

Figures 14, 15:
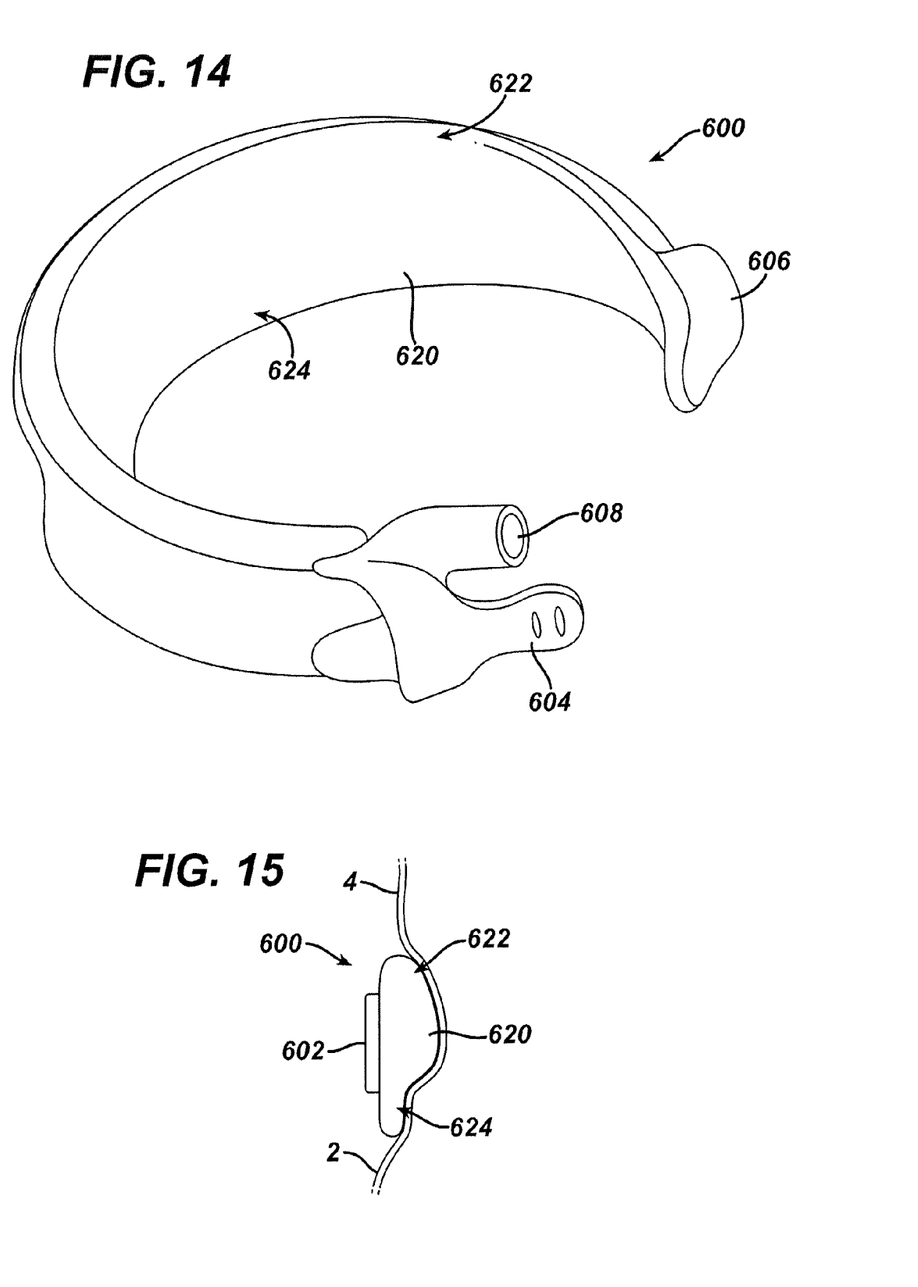
FIG. 14 depicts a perspective view of an exemplary gastric band having a generally asymmetric profile defined by a contoured contact surface with an upper portion that is thicker than a lower portion.
FIG. 15 depicts a cross-sectional view of the gastric band of FIG. 14.

FIGS. 14-15 show a merely illustrative variation of gastric band (500). The exemplary gastric band (600) shown in FIGS. 14-15 is substantially similar to gastric band (500) shown in FIGS. 12-13. In particular, gastric band (600) of this example comprises a flexible strap (602) (not shown in FIG. 14) and a bladder (620). Each end of strap (602) includes a respective buckle member (604, 606), which may be secured to each other when gastric band (600) is sufficiently wrapped about the patient's stomach (2). For instance, buckle members (604, 606) may be constructed an operable in accordance with the teachings of U.S. Pat. No. 7,416,528, entitled "Latching Device for Gastric Band," issued Aug. 26, 2008, the disclosure of which is incorporated by reference herein. Buckle member (604) also includes an integral fluid port (608), which is in fluid communication with the interior of bladder (620) and may be coupled with catheter (18). In addition, while strap (602) is flexible in this example, strap (602) substantially resists stretching along its length, such that bladder (620) expands and exerts inward forces on the gastro-esophageal junction of the patient when fluid is added to bladder (620) (e.g., using a needle inserted through septum (16) of injection port (12), etc.). Of course, strap (602) may have any other suitable configuration.

Like bladder (520) described above, bladder (620) of the present example is also contoured and asymmetric about a horizontal plane (not shown) that bisects gastric band (600). In particular, upper and lower portions (622, 624) of gastric band (600) present a contoured configuration rather than a generally flat or tapered configuration. In the present example, upper portion (622) is generally convex while lower portion (624) is generally flat or even concave, with a curved transition being provided between upper and lower portions (622, 624). Thus, unlike gastric band (500), an upper portion (622) of gastric band (600) presents a profile that is substantially narrower than the profile presented by a lower portion (624) of gastric band (600), such that the stoma passageway provided by gastric band (600) between esophagus (4) and stomach (2) is narrower near the top of gastric band (600) (i.e., the esophagus (4) side) than it is near the bottom of gastric band (600) (i.e., the stomach (2) side). Bladder (620) is preformed to have a "top heavy" contoured configuration in the present example, such that gastric band (600) presents the contoured configuration both when bladder (620) is substantially non-inflated (as seen in FIG. 14) and when bladder (620) is substantially inflated (as seen in FIG. 15). Other suitable ways in which gastric band (600) may be formed will be apparent to those of ordinary skill in the art in view of the teachings herein.

In some settings, and as noted above, unequal distribution of liquid in bladder (620) resulting from the contoured configuration of bladder (620) may provide a stoma passageway provided by gastric band (600) between esophagus (4) and stomach (2) is narrower near the top of gastric band (600) (i.e., the esophagus (4) side) than it is near the bottom of gastric band (600) (i.e., the stomach (2) side). This may allow gastric band system (10) to be used at a lower overall pressure while providing results similar to a higher pressure gastric band system when a food bolus first encounters the stoma passageway. This slowing of the food bolus may result in pouch (6) filling relatively quickly and the patient feeling an early sense of satiation. However, as the food bolus starts to pass through the stoma passageway defined by gastric band (600), the liquid within gastric band (600) may be initially displaced below the food bolus (i.e., from upper portion (622) to lower portion (624)), then eventually back above the food bolus (i.e., from lower portion (624) back to upper portion (622)). In other words, the liquid in bladder (622) may initially be more voluminous in upper portion (622), then in lower portion (624), then back in upper portion (622). In some settings, such shifting of fluid in bladder (620) may assist in passage of food through the stoma passageway while still slowing the passage of food through the stoma passageway.

Figure 16A:
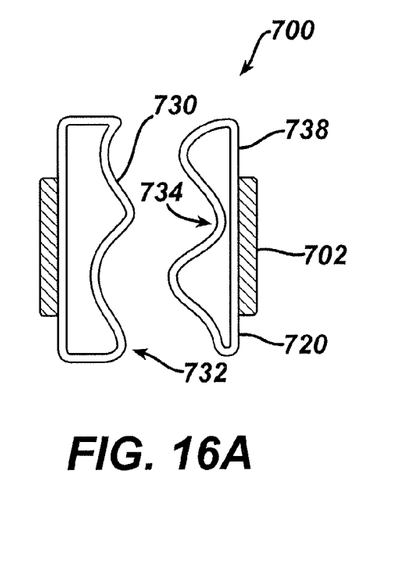
FIG. 16A depicts a cross-sectional view of an exemplary gastric band having a generally asymmetric profile defining a tortuous path, in a substantially non-inflated configuration.
Figure 16B:
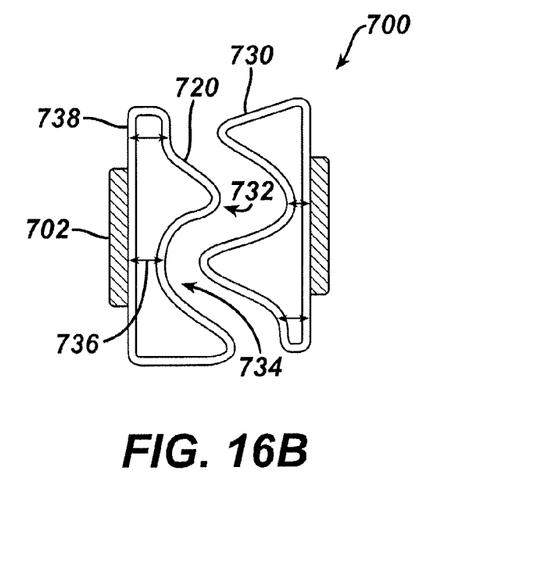
FIG. 16B depicts a cross-sectional view of the gastric band of FIG. 16A, in a substantially inflated configuration.

Another exemplary gastric band (700) is shown in FIGS. 16A-16B. Gastric band (700) of this example comprises a flexible strap (702) and a bladder (720). The ends of strap (702) may be secured relative to each other when gastric band (700) is sufficiently wrapped about the patient's stomach (2). For instance, strap (702) may include buckle features similar to those described in U.S. Pat. No. 7,416,528, entitled "Latching Device for Gastric Band," issued Aug. 26, 2008, the disclosure of which is incorporated by reference herein. In addition, while strap (702) is flexible in this example, strap (702) substantially resists stretching along its length, such that bladder (720) expands and exerts inward forces on the gastro-esophageal junction of the patient when fluid is added to bladder (720) (e.g., using a needle inserted through septum (16) of injection port (12), etc.). Of course, strap (702) may have any other suitable configuration.

Like various bladders described above, bladder (720) of the present example is also substantially asymmetric about a horizontal plane (not shown) that bisects gastric band (700). In particular, the inner wall (730) of bladder (720) has a wavy configuration presenting a series of peaks (732) and valleys (734). When gastric band (700) is installed about a patient's gastro-esophageal junction may substantially conform to the configuration of inner wall (730), such that the peaks (732) and valleys (734) provide a generally tortuous stoma passageway from esophagus (4) to stomach (2). Such a tortuous passageway may substantially slow the passage of food from esophagus (4) to stomach (2), providing the patient with a desirable early sense of satiety, while not creating an undesirable "backup" of food in pouch (6) or esophagus (4) and the undesirable results that may appertain to such a backup of food in pouch (6) or esophagus (4). In some settings, the configuration of peaks (732) and valleys (734) may reduce the likelihood of undesired migration of gastric band (700) along the exterior of esophagus (4) and/or stomach (2).

Bladder (720) of the present example is preformed to include peaks (732) and valleys (734), such that gastric band (700) presents peaks (732) and valleys (734) both when bladder (720) is substantially non-inflated (as seen in FIG. 16A) and when bladder (720) is substantially inflated (as seen in FIG. 16B). In some versions, bladder (720) also includes internal webs (736) or ribs that secure valleys (734) to the opposite wall (738) of bladder (720), thereby restricting the separation of valleys (734) from opposite wall (738) to help ensure presence of valleys (734) even when bladder (720) is fully inflated. Other suitable ways in which gastric band (700) may be formed will be apparent to those of ordinary skill in the art in view of the teachings herein.

Figure 17:
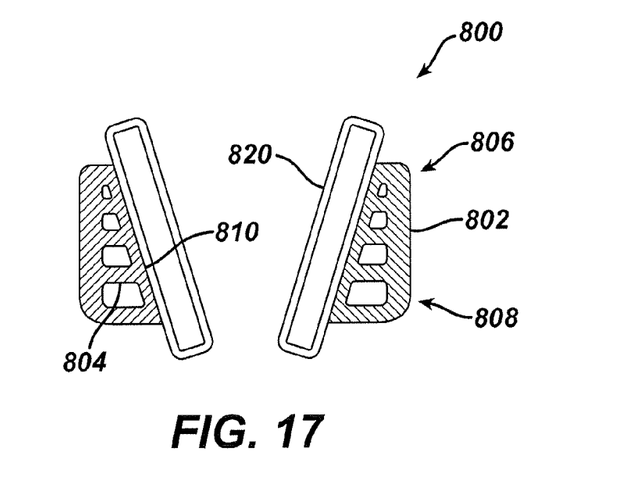
FIG. 17 depicts a cross-sectional view of an exemplary gastric band having a generally asymmetric strap.

Yet another exemplary gastric band (800) is shown in FIG. 17. Gastric band (800) of this example comprises a flexible strap (802) and a bladder (820). The ends of strap (802) may be secured relative to each other when gastric band (800) is sufficiently wrapped about the patient's stomach (2). For instance, strap (802) may include buckle features similar to those described in U.S. Pat. No. 7,416,528, entitled "Latching Device for Gastric Band," issued Aug. 26, 2008, the disclosure of which is incorporated by reference herein. In addition, while strap (802) is flexible in this example, strap (802) substantially resists stretching along its length, such that bladder (820) expands and exerts inward forces on the gastro-esophageal junction of the patient when fluid is added to bladder (820) (e.g., using a needle inserted through septum (16) of injection port (12), etc.).

Bladder (820) of the present example is substantially symmetric. However, gastric band (800) of this example still defines an asymmetric opening due to the configuration of strap (802). In particular, strap (802) is configured such that an upper portion (806) of strap (802) defines an inner diameter that is greater than the inner diameter defined by a lower portion (808) of strap (802) when the ends of strap (802) are secured to each other. This configuration provides an inclined inner surface (810) to which bladder (820) is secured. A plurality of annular ribs (804) assist in maintaining this inclined configuration, even when gastric band (800) is installed in a patient. As seen in FIG. 17, ribs (804) become progressively wider along the height of strap (802). The end result in the present example is tapered engagement between gastric band (800) and the patient's gastro-esophageal junction, such that the stoma passageway is similar to stoma passageway (56) shown in FIG. 8. While bladder (820) is itself substantially symmetrically shaped in the present example, it should be understood that bladder (820) may have any suitable alternative shape. It should also be understood that the tapered configuration defined by strap (802) in the present example is merely illustrative, and that strap (802) may alternatively provide any other suitably shaped profile. Furthermore, it should be understood that ribs (804) and/or other features may provide variably compliance along the height of gastric band (800) (e.g., the strength of ribs (804) may vary along the height of strap (802), etc.). Still other suitable configurations for gastric band (800) will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
    (a) a strap comprising an interior surface and an opposing exterior surface, wherein the strap is sized and configured to wrap along a first plane to encompass an anatomical feature; and
    (b) a single inflatable bladder secured to the interior surface of the strap, wherein the inflatable bladder is shaped such that the inflatable bladder has a cross-sectional profile that is asymmetric about the first plane in both an inflated configuration and a non-inflated configuration, wherein the inflatable bladder is spaced away from and non-foldable about the exterior surface of the strap in both the inflated configuration and the non-inflated configuration, wherein a width of the inflatable bladder measured perpendicular to the first plane is greater than a width of the strap measured perpendicular to the first plane, wherein the inflatable bladder includes an expansion section comprising one or more structures selected from the group consisting of folds, pleats, and gussets, and wherein the expansion section is configured to allow the bladder to transition from a first state in which the bladder has a substantially flat cross-sectional configuration to a second state in which the bladder has a substantially tapered cross-sectional configuration.

2. The apparatus of claim 1, wherein the inflatable bladder includes an upper region generally above the first plane and a lower region generally below the first plane, wherein the lower region has a cross-sectional profile that is wider than the cross-sectional profile of the upper region.

3. The apparatus of claim 2, wherein the inflatable bladder includes an inclined surface extending from the upper region to the lower region, providing the inflatable bladder with a tapered cross-sectional profile.

4. The apparatus of claim 1, wherein the inflatable bladder comprises a wall defining an open space configured to receive a fluid, wherein the wall has a thickness that varies about the perimeter of the bladder.

5. The apparatus of claim 1, wherein the inflatable bladder comprises a wall defining an open space configured to receive a fluid, wherein the expansion section is formed at least in part by the wall.

6. The apparatus of claim 1, wherein the inflatable bladder comprises a wall defining an open space configured to receive a fluid, wherein the wall includes an inner region configured to engage the anatomical feature.

7. The apparatus of claim 6, wherein the inner region of the wall is thicker than one or more other regions of the wall.

8. The apparatus of claim 1, wherein the strap is sized and configured to wrap along a first plane to encompass an esophagus or an upper portion of a stomach, wherein the bladder is configured to create a variably restrictive stoma passageway in the esophagus or upper portion of the stomach.

9. An apparatus, comprising:
(a) a strap comprising an interior surface and an opposing exterior surface, wherein the strap is sized and configured to wrap along a first plane to encompass an anatomical feature; and
(b) a single inflatable bladder secured to the interior surface of the strap, wherein the inflatable bladder is shaped such that the inflatable bladder has a cross-sectional profile that is asymmetric about the first plane in both an inflated configuration and a non-inflated configuration, wherein the inflatable bladder is spaced away from and non-foldable about the exterior surface of the strap in both the inflated configuration and the non-inflated configuration, wherein a width of the inflatable bladder measured perpendicular to the first plane is greater than a width of the strap measured perpendicular to the first plane, wherein the inflatable bladder comprises a wall defining an open space configured to receive a fluid, wherein the wall includes an inner region configured to engage the anatomical feature, and wherein the inner region of the wall is thicker than one or more other regions of the wall.

* * * * *